United States Patent [19]

DeGregorio et al.

[11] Patent Number: 5,750,576
[45] Date of Patent: May 12, 1998

[54] TRIPHENYLETHYLENES FOR THE PREVENTION AND TREATMENT OF OSTEOPOROSIS

[75] Inventors: Michael DeGregorio; Valerie Wiebe, both of Granite Bay, Calif.; Lauri Kangas, Raisio, Finland; Pirkko Härkönen, Turku, Finland; Kalervo Väänänen, Oulu, Finland; Aire Laine, Turku, Finland

[73] Assignee: Orion-Yhtymä Oy, Espoo, Finland

[21] Appl. No.: 793,938
[22] PCT Filed: Sep. 6, 1995
[86] PCT No.: PCT/FI95/00475
  § 371 Date: Apr. 1, 1997
  § 102(e) Date: Apr. 1, 1997
[87] PCT Pub. No.: WO96/07402
  PCT Pub. Date: Mar. 14, 1996

[30] Foreign Application Priority Data

Sep. 7, 1994 [GB] United Kingdom ............... 9418067

[51] Int. Cl.$^6$ ............................................. A61K 31/075
[52] U.S. Cl. ............................................. 514/720
[58] Field of Search ................................. 514/720

[56] References Cited

U.S. PATENT DOCUMENTS 5,605,700 2/1997 DeGregorio ............... 424/448

OTHER PUBLICATIONS

"Anti–Oestrogens Induce the Secretion of Active Transforming Growth Factor Beta From Human Fetal Fibroblasts", *Br. Journal Cancer*, A.A. Colletta et al., vol. 62, pp. 405–409, (1990).

"Biochemical and Pharmacological Effects of Toremifene Metabolites", *Cancer Chemotherapy and Pharmacology*, Lauri Kangas, vol. 27, No. 1, pp. 8–12, 1990.

"Agnostic and Antagonistic Effects of Antiestrogens in Different Target Organs", *Acta Oncologica*, Lauri Kangas, vol. 31, No. 2, pp. 143–146, 1992.

"Phase I Clinical and Pharmacokinetics Study of High–Dose Toremifene in Postmenopausal Patients with Advanced Breast Cancer", *Cancer Chemotherapy and Pharmacology*, James Bishop et al., vol. 30, pp. 174–178, 1992.

"In Vitro and In Vivo Binding of Toremifene and Its Metabolites in Rat Uterus", *The Journal of Steroid Biochemistry*, Niklas Simberg et al., vol. 36, No. 3, pp. 197–202, 1990.

"Effects of Anti–estrogens on Bone in Castrated and Intact Female Rats", *Breast Cancer Research and Treatment*, V. Craig Jordan et al., vol. 10, No. 1, 1987, pp. 31–35.

"Metabolism of Toremifene in the Rat", *The Journal of Steroid Biochemistry*, Hannu Sipilä et al., vol. 36, No. 3, pp. 211–215, 1990.

"Pharmacokinetics of Toremifene", *The Journal of Steroid Biochemistry*, M. Anttila et al., vol. 36, No. 3, pp. 249–252, 1990.

*Primary Examiner*—Theodore J. Criares
*Attorney, Agent, or Firm*—Burns, Doane, Swecker & Mathis, L.L.P.

[57] ABSTRACT

Compounds having formula (I) wherein $R_1$ and $R_2$ are independently H or OH, are useful in the treatment and prevention of osteoporosis. The compounds of formula (I) are devoid of significant antiestrogenic and estrogenic activity.

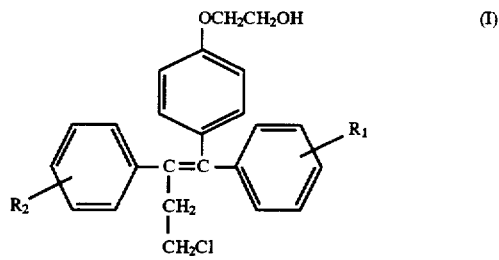

6 Claims, 1 Drawing Sheet

TRIPHENYLETHYLENES FOR THE PREVENTION AND TREATMENT OF OSTEOPOROSIS

This application is a 371 of PCT/FI95/00475 filed Sep. 6, 1995.

This invention relates to the use of certain triphenylethylene compounds, that are devoid of significant antiestrogenic and estrogenic activity, for the prevention and treatment of osteoporosis.

Osteoporosis is one of the most common chronic diseases in postmenopausal women. It is characterized by rapid bone loss after the menopause resulting in bone fractures. One of the major factors in the pathogenesis of osteoporosis is increased bone resorption in association with estrogen-deficiency. Increased bone resorption results in decreased bone mass and decreased bone strength. The current preventive treatment includes the use of estrogen replacement therapy in postmenopausal women.

Estrogen and transforming growth factors-β (TGF-β) are key factors in bone remodelling and may have overlapping functions. They are both capable of inducing collagen and inhibiting bone resorption. It is still unclear whether estrogen functions through a pathway that regulates TGF-β production.

Postmenopausal bone loss occurs when coupling between bone formation and bone resorption is no longer balanced. Estrogen replacement therapy results in decreased bone turnover, decreased bone resorption and decreased fracture occurrence in postmenopausal patients. However, results of in vitro experiments have not provided clear-cut clues to the mechanism by which estrogen exerts its effects on bone. Data suggest that estrogen may act on bone by several mechanisms, either directly through estrogen receptors, indirectly through other cells besides bone cells and/or in concert with other factors and hormones such as progesterones. A long-term use of estrogens is associated with potential side effects due to the increased risk for cancers of estrogen dependent tissues such as endometrium and breast.

Triphenylethylene group antiestrogens tamoxifen and toremifene have recently been shown to stimulate TGF-β production by fibroblasts (Colletta et al., Br. J. Cancer, 62, 405–409, 1990. Tamoxifen has also been shown to have a positive effect on bone density (Jordan et al, Breast Cancer Res. Treatm, 10, 31–35, 1987). Tamoxifen and toremifene are both in a group of compounds that are used clinically for the treatment of estrogen receptor positive breast cancer. In patients with breast cancer these compounds primarily exert their antiestrogenic properties by blocking the estrogen receptors present in breast cancer cells, thus inhibiting cancer cell growth. Although their primary mode of action is inhibition of estrogen receptors they are also known to behave as estrogen agonists, particularly in uterine tissue in which they stimulate cell proliferation. Several reports have now suggested that tamoxifen may in fact induce secondary uterine tumors in women receiving long term tamoxifen therapy. The antiestrogenic triphenylethylenes also share many hormonal side effects in common with the estrogens, including hot flashes, nausea, menstrual irregularity and the potential for development of life-threatening thrombolic disorders.

While the clinical efficacy of tamoxifen as an agent to prevent and/or treat osteoporosis remains to be elucidated, the side effects of the antiestrogenic triphenylethylenes would be a particular disadvantage for type of long term, chronic therapy that is required to prevent osteoporosis. On the other hand agents, that had the ability to prevent osteoporosis but were devoid of hormone related side effects such us uterine hyperplasia, hot flashes, nausea and thromboembolic complications would be very useful clinically.

Figure 1:
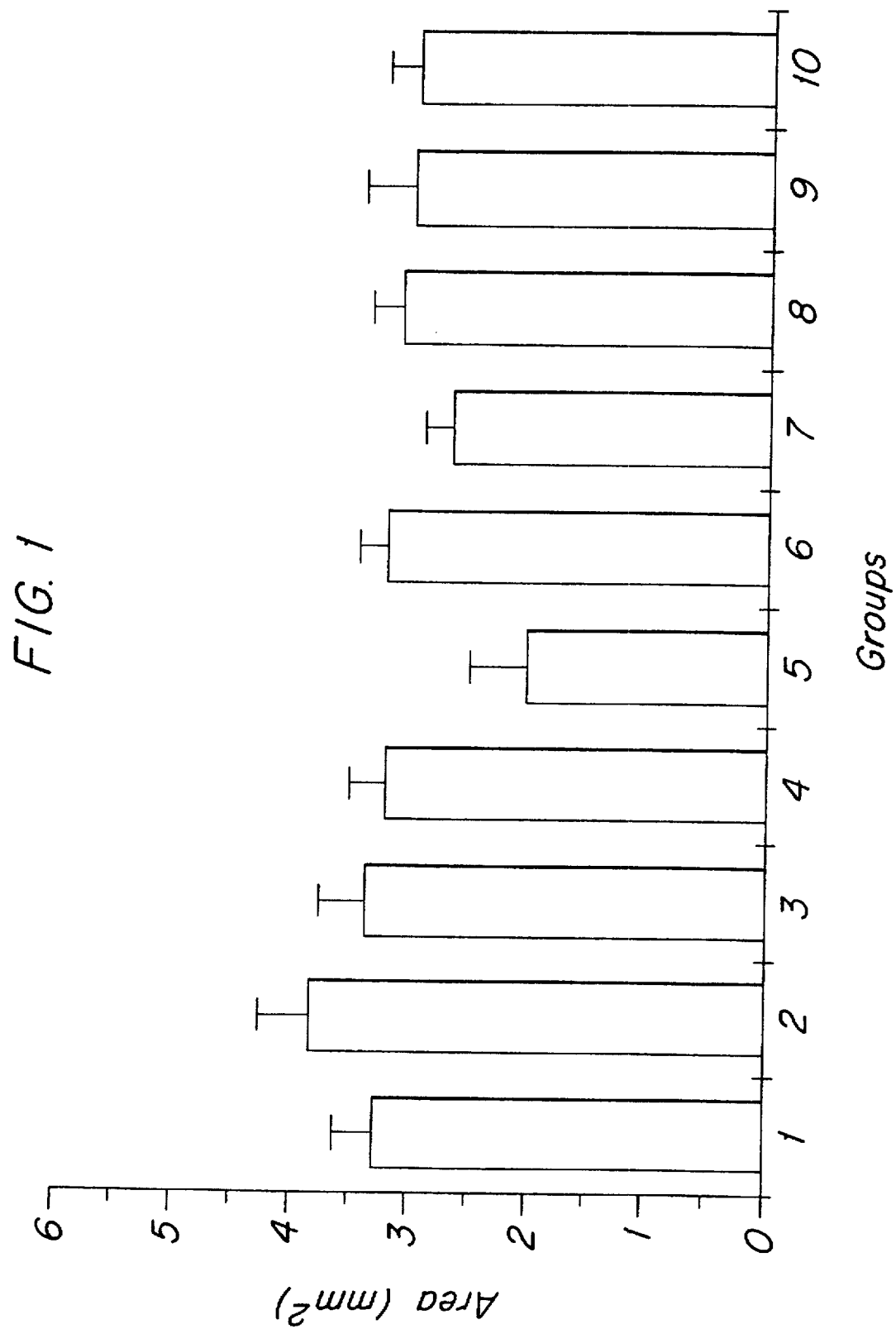
FIG. 1 illustrates the results of the measurements of ash weight of the epiphysis of rat tibia of compound A.

According to the invention a compound having formula (I)

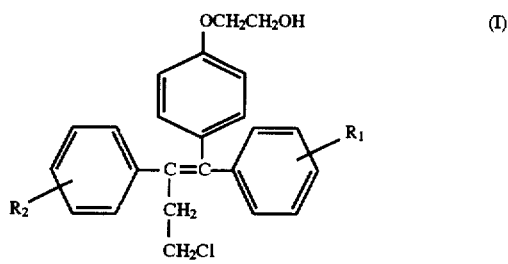

wherein $R_1$ and $R_2$ are independently H or OH, is used in the manufacture of a medicament for use in the prevention and treatment of osteoporosis. It has been found that the compounds of formula (I), which are devoid of significant antiestrogenic and estrogenic activity, effectively inhibit the ovarectomy-induced loss of bone mineral contents and increase bone strength in rats. It has also been discovered that the compounds of formula (I) stimulate the production of TGF-β by bone cells. The stimulation activity of the compounds according to the invention is greater than that of tamoxifen or toremifene and equals the activity of estrogen. Furthermore the compounds of formula (I) may enhance the useful properties of estrogen while blocking the adverse effects of estrogen on endometrial tissue when used in combination. Unlike estrogen or partial antiestrogens, the compounds of formula (I) lack significant hormone associated side effects. Therefore the compounds of formula (I) are especially suitable for use in the prevention and treatment of osteoporosis.

The term osteoporosis means here postmenopausal or involutional osteoporosis and other bone diseases, which are characterized by loss of bone mass.

The preferred compounds of the invention are (deaminohydroxy)toremifene or 2-[4-(4-chloro-1,2-diphenyl-but-1-enyl)phenoxy]ethanol), 4-hydroxy (deaminohydroxy)toremifene or 4-[4-chloro-1-[4-(2-hydroxyethoxy) phenyl]-2-phenyl-but-1-enyl]phenol) and 4,4'-dihydroxy(deaminohydroxy)toremifene or 4-[4-chloro-1-[4-(2-hydroxyethoxy) phenyl]-2-(4-hydroxyphenyl)but-1-enyl]phenol:

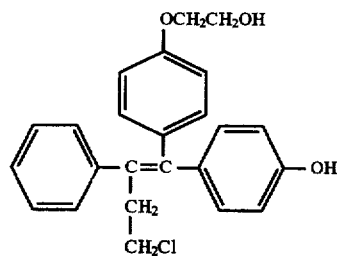

4-hydroxy(deaminohydroxy)toremifene

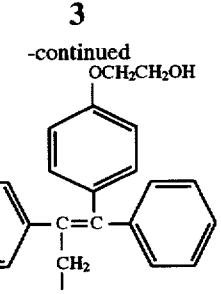

(deaminohydroxy)toremifene

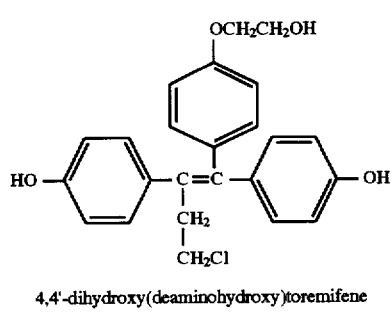

4,4'-dihydroxy(deaminohydroxy)toremifene

These compounds are metabolites of toremifene and have been described earlier in Kangas L., "Biochemical and pharmacological effect of toremifene metabolites", Cancer Chemother. Pharmacol., (1990), 27, 8–12 and Sipilä H. et al., "Metabolism of toremifene in the rat", J. Steroid Biochem., 36,3,211–215, (1990). However, it has not been known that these compounds are useful for treating or preventing osteoporosis. The compounds of formula (I) can be prepared using methods known in the art.

The invention provides a method for treating or preventing osteoporosis which method comprises administering a pharmaceutically active amount of a compound of formula (I) to a patient in need of such treatment.

The compounds of the invention may be administered alone or together with other active compounds. The experimental data shows that the compounds of formula (I) may decrease the adverse effects of estrogen on endometrial tissue when used in combination. Therefore the invention also comprises the use of compounds of formula (I) together with an estrogen, such as β-estradiol, in treating or preventing osteoporosis.

The present invention also provides the use of a compound of formula (I) in the manufacture of a medicament for use in the prevention or treatment of osteoporosis.

The invention also provides a pharmaceutical composition for use in treating or preventing osteoporosis, which composition comprises a therapeutically effective amount of a compound of formula (I).

The compound of formula (I) may be administered in a variety of ways including orally, parenterally or transdermally using conventional forms of preparations, such as capsules, tablets, granules, powders, suppositories, injections, patches, suspensions and syrups. The compounds of the invention may be administered monthly, weekly or daily or several times a day depending upon the patient's needs. A typical daily oral dosage is within the range of from about 0.5 mg to about 1000 mg, preferably from about 1 mg to about 500 mg, more preferably from about 5 mg to about 100 mg, of the active compound. However, the dosage may be properly varied depending on the age, body weight and conditions of the patient as well as on the administration method.

The compositions according to the invention can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutical effect, for example about 0.5 to 1000 mg, preferably about 1 mg to 500 mg, more preferably about 5 mg to 100 mg, in unit dosage form for both oral and parenteral administration.

The following examples illustrate the synthesis of the compounds of the invention.

EXAMPLES

Example 1

Z-4-[4-(2-benzyloxyethoxy)-phenyl]-3,4-diphenyl-but-3-en-1-ol

The reaction vessel was charged with toluene (790 ml), 48% aqueous sodium hydroxide (790 ml), tetrabutylammonium bromide (2.12 g, 6.6 mmol) and Z-4-(4-hydroxy-1,2-diphenyl-but-1-enyl)-phenol (50 g, 0.16 mol) prepared by the method described by U.S. Pat. No. 4,996,225. The mixture was refluxed for 30 minutes. Benzyl-(2-bromoethyl) ether (Grobelny D. et al., Tetrahedron Letters 28, 2639–42, 1979) (41.7 g, 0.19 mol) was added to the reaction mixture and the refluxing was continued for 2 hours. Then the mixture was cooled to room temperature, layers were separated and aqueous phase was washed with toluene. Toluene phases were combined, washed with water, dried and evaporated to dryness. The residue was used in the next stage without further purification.

$^1$H NMR (300 MHz, CDCl$_3$):d 1.2 (1H, t, OH), 2.8 (2H, t, CH$_2$—C=), 3.6 (2H, dt, CH$_2$OH), 3.7 (2H, t, CH$_2$OBn), 4.0 (2H, t, CH$_2$OPh), 4.6 (2H, s, OCH$_2$Ph), 6.6 (2H, d, H—PhO), 6.8 (2H, d, H—PhO), 7.1–7.4 (15H, m, H—Ph).

Example 2

Z-1-[4-(2-benzyloxyethoxy)-phenyl]-4-chloro-1,2-diphenyl-but-1-ene

Z-4-[4-(2-benzyloxyethoxy)-phenyl]-3,4-diphenyl-but-3-en-1-ol prepared in the previous stage was dissolved in acetonitrile (400 ml). Triphenyl phosphine (103.5 g, 0.4 mol) and tetrachloromethane (120 g, 0.79 mol) were added and the mixture was refluxed for 2 hours. Then the mixture was evaporated to dryness under reduced pressure. The residue was dissolved in methanol (160 ml) and water (40 ml) and extracted three times with petroleum ether (3×200 ml) at boiling point. Petroleum ether layers were combined and evaporated to dryness under reduced pressure. The residue was crystallized twice from ethanol (700 ml). Yield 36 g.

$^1$H NMR (300 MHz, CDCl$_3$):d 2.9 (2H, t, CH$_2$—C=), 3.4 (2H, dt, CH$_2$Cl), 3.7 (2H, t, CH$_2$OBn), 4.0 (2H, t, CH$_2$OPh), 4.6 (2H, s, OCH$_2$Ph), 6.6 (2H, d, H—PhO), 6.8 (2H, d, H—PhO, 7.1–7.4 (15H, m, H—Ph).

Example 3

Z-2-[4-(4-chloro-1,2-diphenyl-but-1-enyl)-phenoxy]-ethanol

Z-1-[4-(2-benzyloxyethoxy)-phenyl]-4-chloro-1,2-diphenyl-but-1-ene (36 g, 0.08 mol) was dissolved in the mixture of ethyl acetate (350 ml) and ethanol (350 ml). Palladium on carbon (5%, 0.28 g) was added and the solution was flushed with hydrogen gas until there was not any starting compound left (thin layer chromatography). Palladium on carbon was filtered off through siliceous earth and the filtrate was evaporated. The residue was crystallized from the mixture of ethanol (155 ml) and water (65 ml). Yield 20 g.

¹H NMR (300 MHz, CDCl₃):d 2.9 (2H, t, CH₂—C=), 3.4 (2H, dt, CH₂Cl), 3.84–3.89 (2H, m, CH₂OH), 3.92–3.96 (2H, m, CH₂OPh), 6.6 (2H, d, H—PhO), 6.8 (2H, d, H—PhO), 7.1–7.4 (10H, m, H—Ph).

Example 4

Z-4-[4-(2-benzyloxyethoxy)-phenyl]-4-(4-benzyloxyphenyl)-3-phenylbut-3-en-1-ol

The reaction vessel was charged with sodium hydride (0.43 g, 0.0178 mol) and dimethyl formamide (34 ml). 4-[1-(4-Benzyloxyphenyl)-4-hydroxy-2-phenyl-but-1-enyl] pheno (5 g, 0.0118 mol) prepared by the method of U.S. Pat. No. 4,996,225 was dissolved to dimethyl formamide (6 ml), added to the mixture at room temperature and stirring was continued for half an hour. Then benzyl-(2-bromoethyl)ether (3.06 g, 0.014 mol) was added dropwise during 20 minutes to the reaction mixture and stirring was continued for additional 4 hours. The reaction mixture was poured into brine and extracted with ethyl acetate. Organic layer was washed with 2 N hydrogen chloride solution and twice with water, dried and evaporated to dryness. The product was purified by flash chromatography (toluene:methanol, 9.8:0.2). Yield 2.8 g.

¹H NMR (300 MHz, CDCl₃): d 2.78 (2H, t, CH₂—C=), 3.59 (2H, t, CH₂OH), 3.83–3.86 (2H, m, CH₂OBn), 4.15–4.19 (2H, m, CH₂OPh), 4.65 (2H, s, CH₂OCH₂Ph), 6.79 (2H, d, H—PhO), 6.9 (2H, d, H—PhO), 7.11–7.37 (17H, m, H—PhO, H—Ph).

Example 5

Z-1-[4-(2-benzyloxyethoxy)-phenyl]-1-(4-benzyloxyphenyl)-4-chloro-2-phenylbut-1-ene 4-[4-(2-benzyloxyethoxy)-phenyl]-4-(4-benzyloxyphenyl)-3-phenylbut-3-en-1-ol (1.9 g, 3.45 mmol), triphenyl phosphine (1.8 g, 6.9 mmol), carbon tetrachloride (2.6 g, 17.25 mmol) and acetonitrile (10 ml) were stirred at room temperature for an hour. The product was separated by the same method as Z-1-[4-(2-benzyloxyethoxy)-phenyl]-4-chloro-1,2-diphenyl-but-1-ene described in example 2 and purified by flash chromatography (toluene: methanol, 9.75:0.25). Yield 1.2 g.

¹H NMR (300 MHz, CDCl₃):d 2.96 (2H, t, CH₂—C=), 3.42 (2H, t, CH₂ Cl), 3.72–3.75 (2H, m, CH₂OBn), 3.99–4.02 (2H, m, CH₂OPh), 4.58 (2H, s, CH₂OCH₂Ph), 5.07 (2H, s, PhOCH₂Ph), 6.57 (2H, d, H—PhO), 6.77 (2H, d, H—PhO), 6.98 (2H, d, H—PhO), 7.10–7.47 (17H, m, H—Ph, H—PhO).

Example 6

Z-4-[4-chloro-1-[4-(2-hydroxyethoxy)phenyl]-2-phenyl-but-1-enyl]phenol

1-[4-(2-Benzyloxyethoxy)-phenyl]-1-(4-benzyloxyphenyl)-4-chloro-2-phenylbut-1-ene (1.0 g, 1.74 mmol) was debenzylated by the same method as Z-1-[4-(2-benzyloxyethoxy)-phenyl]-4-chloro-1,2-diphenyl-but-1-ene described in example 3. The residue was crystallised from the mixture of ethanol and water (1:1). Yield 0.3 g.

¹H NMR (300 MHz, CDCl₃):d 2.95 (2H, t, CH₂—C=), 3.42 (2H, t, CH₂Cl), 3.86–3.91 (2H, m, CH₂OH), 3.94–3.97 (2H, m, CH₂OPh), 6.56(2H, d, H—PhO), 6.78 (2H, d, H—PhO), 6.83 (2H, d, H—PhO), 7.11–7.22 (7H, m, H—Ph, H—PhO).

Example 7

Z,E-4-[4-(2-benzyloxyethoxy)phenyl]-3,4-bis-(4-benzyloxyphenyl)-but-3-en-1-ol

4-[1,2-Bis-(4-benzyloxyphenyl)-4-hydroxy-but-1-enyl] phenol (2 g, 3.8 mmol) (prepared from 4-benzyloxy-4'-tetrahydropyranyloxy benzophenone and 4-benzyloxycinnamic acid ethyl ester by the method described in U.S. Pat. No. 4,996,225, potassium carbonate (1.5 g, 1.13 mmol), KI (catalytic amount) and ethanol (40 ml) were refluxed for 15 min. Benzyl-(2-bromoethyl)ether (Grobelny D. et al., Tetrahedron Letters 28, 2639–42, 1979) (1.1 g, 4.6 mmol) was added dropwise to the reaction mixture during half an hour and refluxing was continued for additional 2 hours. Then extra portion of potassium carbonate (0.78 g, 0.57 mmol) and benzyl-(2-bromoethyl)ether (0.5 g, 2.3 mmol) was added to the reaction mixture and refluxing was continued for 2 hours. After completion of the reaction the mixture was filtered, filtrate was evaporated to dryness under reduced pressure and the residue was purified by flash chromatography (toluene:methanol, 9.9:0.1). Yield 2.2 g.

¹H NMR (80 MHz, CDCl₃+CD₃OD):d 2.75 (2H, t, CH₂—C=), 3.57 (2H, t, CH₂OH), 3.75–3.91 (2H, m, CH₂OBn), 4.01–4.23 (2H, m, CH₂OPh), 4.58 and 4.64 (2H, s, (CH₂OCH₂Ph), 4.93 and 5.0 and 5.1 (4H, s, PhOCH₂Ph), 6.5–7.45 (27H, m, H—PhO, H—Ph).

Example 8

Z,E-1-[4-(2-benzyloxyethoxy)phenyl]-1,2-bis-(4-benzyloxyphenyl)-4-chloro-but-1-ene 1-[4-(2-benzyloxyethoxy)phenyl]-1,2-bis-(4-benzyloxyphenyl)-4-chlorobut-1-ene was prepared from 4-[4-(2-benzyloxyethoxy)phenyl]-3,4-bis-(4-benzyloxypheny)-but-3-en-1-ol (0.65 g, 0.98 mmol), triphenyl phosphine (0.5 g, 1.96 mmol) and carbon tetrachloride (0.74 g, 4.9 mmol) by the method described in example 2. The product was purified by flash chromatography (toluene). Yield 0.42 g.

¹H NMR (80 MHz, CDCl₃ +CD₃OD):d2.92 (2H, t, CH₂—C=), 3.43 (2H, t, CH₂Cl), 3.74–4.18 (4H, m, OCH₂CH₂O), 4.59 and 4.64 (2H, s, CH₂OCH₂Ph), 4.93 and 5.0 and 5.07 (4H, s, PhOCH₂ Ph), 6.6–7.5 (27H, m, H—PhO, H—Ph).

Example 9

Preparation of Z,E-4-[4-chloro-1-[4-(2-hydroxyethoxy) phenyl]-2-(4-hydroxyphenyl)but-1-enyl]phenol 1-[4-(2-benzyloxyethoxy)phenyl]-1,2-bis-(4-benzyloxyphenyl)-4-chlorobut-1-ene (0.4 g, 0.66 mmol) was debenzylated by the method described in example 3 despite of the temperature, which was 40° C. in this reaction. The product was purified by flash chromatography (toluene:methanol, 9.4:0.6). Yield 0.18 g.

H NMR (300 MHz, CD₃OD):d 2.86 and 2.88 (2H, t, CH₂—C=), 3.41 (2 H, t, CH₂Cl), 3.77–4.07 (4H, m, OCH₂CH₂OH), 6.44 (2H, d, H—PhO), 6.58–7.17 (12H, m, H—PhO).

The following experiments illustrate the effects of the compounds of the invention.

EXPERIMENTS

Effects on the Production of TGFβ

Analysis of latent TGFβ produced by osteoblast derived osteosarcoma cells (ROS 17/2.8) cells and UMR-106 cells were performed by analysis of mRNA using northern blot analysis. In addition, different forms of TGFβ were analyzed by HPLC, western analysis and immuno-precipitation. The results are shown in Table 1. Clearly, compounds A and C are very active in producing the release of TGFβ and appear to be as active as estrogen.

Compound A=(deaminohydroxy)toremifene
Compound C=4-hydroxy(deaminohydroxy)toremifene

TABLE 1

Effects of β-estradiol, the antiestrogens tamoxifen and toremifene, and compounds A and C on the production of latent TGFβ by osteosarcoma cells ROS 17/2.8 and UMR-106.

| Cell line | Agents | $10^{-7}$ M |
|---|---|---|
| ROS 17/2.8 | β-estradiol | 1.1 |
| | tamoxifen | 0.6 |
| | toremifene | 0.6 |
| | compound A | 1.6 |
| | compound C | 1.7 |
| UMR-106 | β-estradiol | 1.8 |
| | tamoxifen | 1.1 |
| | toremifene | 1.3 |
| | compound A | 1.5 |
| | compound C | 1.6 |

Data is expressed as treated/control ratios.
All determinations are the average of triplicate samples.

Effects on the Growth of Estrogen Receptor Positive and Negative Breast Cancer Cells This experiment was performed to prove that the concentrations that produce latent TGFβ by the osteoblast-like cells by compounds A and C are independent of hormone action. Breast cancer cell lines MCF-7 ER+ and MDA-MB-231 ER- were used in the experiment. Also a negative control, compound B, was used. Compound B has the essential amine group that has been shown as necessary for antiestrogenic activity (see Jordan et al., "Importance of the alkylaminoethoxy side-chain for the estrogenic and antiestrogenic actions of tamoxifen an trioxifene in the immature rat uterus", Molecular and Cellular Endocrinology, 27, 291–306, 1982). Although complete removal of the alkylaminoethoxy side-chain will produce an estrogen like compound, compounds A and C are stable and not susceptible to this cleavage.

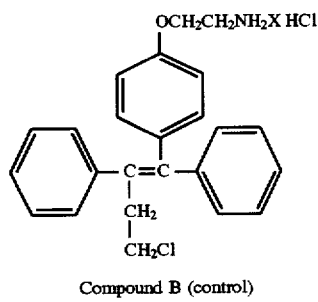

Compound B (control)

Table 2 shows the results of exposing estrogen, compound A, B, C, and combinations of both when exposed to the estrogen receptor positive breast cancer cells MCF-7. The results show that estrogen alone appeared to stimulate the growth of cells whereas compounds A, B and C lack such activity. Clearly, control compound B has an antiestrogen effect that is partially blocked by estrogen. Compounds A and C had little effect on cells alone and a net stimulatory activity similarly to estrogen alone when used in combination with estrogen. This result suggest that compounds A and C at $10^{-7}$M had not significant antiestrogenic activity.

All compounds had little to no effect on the growth of estrogen receptor negative breast cancer cells MDA-MB-231.

TABLE 2

Effect of compounds A, B, C ± Estradiol (E2) on MCF-7 ER+

| Treatment | Percent Survival ± SD |
|---|---|
| Control | 100.00 |
| E2 ($10^{-9}$ M) control | 104.62 ± 0.72 |
| Compound A ($10^{-7}$ M) | 89.68 ± 3.91 |
| Compound A + E2 | 97.70 ± 4.62 |
| Compound B ($10^{-7}$ M) | 47.22 ± 4.04 |
| Compound B + E2 | 90.73 ± 3.07 |
| Compound C ($10^{-7}$ M) | 85.57 ± 2.07 |
| Compound C + E2 | 99.80 ± 4.90 |

The ability of compound A to inhibit the antiestrogenic activity of tamoxifen was also studied. The results (TABLE 3) show that compound A does not inhibit the antiestrogenic activity of tamoxifen. This, together with the fact that the compounds of the invention did not stimulate or inhibit MCF-7 growth, is a further evidence of a non-hormonal mechanism of the compounds of the invention.

TABLE 3

MCF-7 growth inhibition by tamoxifen and tamoxifen + compound A

| Tamoxifen (μM) | Percent survival |
|---|---|
| 0.1 | 89.1 |
| 0.5 | 53.6 |
| 1.0 | 46.1 |
| 2.0 | 43.8 |
| 5.0 | 27.2 |

| Tamoxifen (μM) + A ($10^{-7}$ M) | Percent survival |
|---|---|
| 0.1 | 80.4 |
| 0.5 | 56.9 |
| 1.0 | 50.6 |
| 2.0 | 40.9 |
| 5.0 | 23.7 |

Uterine Effects

This study examined the uterine effects of compounds A, B, C and estrogen in the ovariectomized rat. It was further examined whether compound A could effectively block the uterotrophic effects of estrogen.

40 Sprague-Dawley female rats, 92 days old, were used. Bilateral ovariectomies were performed after anesthestizing the animals with metaphane. Sham surgery was performed by exteriorizing the ovaries but not removing them. The compounds were delivered in a vehicle of 95% corn oil and 5% benzyl alcohol by subcutaneous injection at 250 μl/day. All treatments were initiated the first day after surgery for 21 days. The animals were also injected for fluorochrome labeling at 14 days before sacrifice and tetracycline hydrochloride (25 mg/kg) at 6 days before sacrifice. The pre and post weights of the animals were taken and the animals exsanquinated. The uteri were removed and weighed. The bones were fixed in 70 % ethanol for histological examination. The blood, uteri and one humerus from each animal were assayed for hormone levels and one tibia for histological quantitation of trabecular bone volume.

Table 4 shows that the uterotrophic effects of estrogen were counteracted by compound A. This is new evidence that a non-antiestrogenic agent, which can not be metabolized to an antiestrogenic compound can effectively block the adverse effects of estrogen on the uterus. It is very likely that TGFβ may inhibit the uterine growth despite the estrogenic properties of estrogen.

TABLE 4

Effect of compounds A, B, C ± Estradiol (E2) on rat uterus

| Treatment | Average uterine weight (g) ± SD (n = 6) |
|---|---|
| Sham control | 0.7176 ± 0.0896 |
| E2 control | 0.7140 ± 0.1560 |
| Compound A | 0.3112 ± 0.0460 |
| Compound A + E2 | 0.3540 ± 0.0600 |
| Compound B | 0.3270 ± 0.0840 |
| Compound C | 0.3656 ± 0.0450 |

Effects on Bones

The inhibitory effect of compound A on the ovarectomy-induced loss of bone mineral contents was demonstrated by measuring the ash weight of the epiphysis of rat tibia and by determining the volume of trabecular bone in distal femur by morphometric analysis. The results are presented in Table 5 and FIG. 1. The treatment groups 1–10 of FIG. 1 are the same as those in Table 5.

TABLE 5

Effect of compound A on the ash weight of rat left tibia

| Treatment (4 weeks as indicated) | Ash weight (mg) n = 10 |
|---|---|
| 1. Normal control | 284.2 ± 13.7* |
| 2. + 17β-E2 (sc, 30-day pellet) | 295.0 ± 17.7* |
| 3. + Compound A 1 mg/kg/day (po) | 287.9 ± 12.1* |
| 4. + Compound A 10 mg/kg/day (po) | 292.0 ± 13.6* |
| 5. Ovarectomized control | 259.9 ± 14.6 |
| 6. + 17β-E2 (sc) | 293.2 ± 20.0* |
| 7. + Compound A 1 mg/kg/day | 263.9 ± 16.6* |
| 8. + Compound A 1 mg/kg/day + 17β-E2 | 279.6 ± 16.9* |
| 9. + Compound A 10 mg/kg/day | 276.3 ± 15.9* |
| 10. + Compound A 10 mg/kg/day + 17β-E2 | 285.5 ± 15.6* |

*significantly different from ovarectomized control, $p < 0.05$

The beneficial effect of compound A on trabecular bone mineral contents and volume proportion were associated with increased bone strength in femoral neck and lumbar vertebrae. This was demonstrated by measuring resistance against torsion and compression, respectively (Table 6).

TABLE 6

Effect of compound A on the mechanical strenght of rat femoral neck and L4 vertebra

| Treatment (4 weeks as indicated) | Strength of femoral neck (N) | Compression of L4 (N) |
|---|---|---|
| Normal control | 106.2 ± 18.3[1] | 516.8 ± 75.6 |
| + 17β-E2 (sc, 30-day pellet) | 101.9 ± 20.0 | 657.3 ± 64.0[3,4] |
| + A 1 mg/kg/day (po) | 103.1 ± 14.6[2] | 619.6 ± 114.4[3,4] |
| + A 10 mg/kg/day (po) | 101.0 ± 12.3 | 628.9 ± 108.7[3,4] |
| Ovarectomized control | 86.8 ± 13.4 | 449.7 ± ±83.0 |
| + 17β-E2 (sc) | 120.7 ± 18.1[3] | 582.7 ± 91.8[2] |
| + A 1 mg/kg/day | 87.8 ± 15.2 | 592.4 ± 64.0[3] |
| + A 1 mg/kg/day + 17β-E2 | 100.2 ± 20.5 | 619.6 ± 82.1[3] |
| + A 10 mg/kg/day | 103.7 ± 12.7[1] | 549.4 ± 81.8[1] |
| + A 10 mg/kg/day + 17β-E2 | 115.1 ± 18.3[2] | 641.8 ± 64.6[3,5] |

[1]Significantly different from ovarectomized control, $p < 0.05$
[2]Control, $p < 0.01$
[3]Control, $p < 0.001$
[4]Significantly different from normalcontrol, $p < 0.001$
[5]Significantly different from ovarectomized control treated with A 10 mg/kg/day $p < 0.05$ In another in vivo study using ovariectomized rat model it was found that compound A was as effective as β-estradiol at preventing bone loss while having little effect on the uterus. When compound A was administered in combination with β-estradiol, a greater increase in percent trabecular bone volume were observed when compared to either compound alone and compound A effectively blocked the effects of estrogen on the uterus. The result of this study is presented in Table 7.

TABLE 7

Inhibition of ovariectomy-induced bone loss by compounds A, B, estradiol, and compound A plus estradiol.

| Treatment group | % Trabecular bone volume (n = 3) |
|---|---|
| compound A | 25.24 ± 6.61 |
| compound B | 8.18 ± 5.83 |
| Estradiol | 22.6 ± 5.56 |
| A + E | 38.4 ± 8.14 |

We claim:

1. A method of using a compound of formula (1)

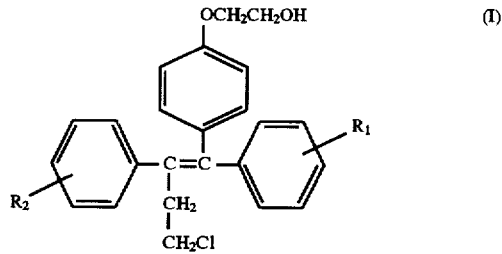

wherein $R_1$ and $R_2$ are independently H or OH, for the treatment or prevention of osteoporosis, comprising administering to a subject in need of such treatment a prophylactically or therapeutically effective amount of a compound of formula (1) as defined above.

2. A method according to claim 1, in which the compound of formula (1) is (deaminohydroxy)toremifene.

3. A method according to claim 1, in which the compound of formula (1) is 4-hydroxy (deaminohydroxy)toremifene.

4. A method according to claim 1, in which the medicament comprises an estrogen.

5. A method according to claim 2, in which the medicament comprises an estrogen.

6. A method according to claim 3, in which the medicament comprises an estrogen.

* * * * *

UNITED STATES PATENT AND TRADEMARK OFFICE
CERTIFICATE OF CORRECTION

PATENT NO. : 5,570,576

DATED : May 12, 1998

INVENTOR(S) : Michael DeGregorio et al.

It is certified that error appears in the above-identified patent and that said Letters Patent is hereby corrected as shown below:

At Column 2, lines 47 to 48, change "2-[4-(4-chloro-1,2-diphenyl-but-1-enyl)phenoxy]ethanol)" to --Z-2-[4-(4-chloro-1,2-diphenyl-but-1-enyl)phenoxy]ethanol)--.

At Column 2, lines 49 to 50, change "4-[4-chloro-1-[4-(2-hydroxyethoxy) phenyl]-2-phenyl-but-1-enyl]phenol)" to --Z-4-[4-chloro-1-[4-(2-hydroxyethoxy) phenyl]-2-phenyl-but-1-enyl]phenol)--.

At Column 2, lines 51 to 52, change "4-[4-chloro-1-[4-(2-hydroxyethoxy) phenyl]-2-(4-hydroxyphenyl)but-1-enyl]phenol" to --Z-4-[4-chloro-1-[4-(2-hydroxyethoxy) phenyl]-2-(4-hydroxyphenyl)but-1-enyl]phenol--.

Signed and Sealed this

Sixth Day of October, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,750,576

DATED         : May 12, 1998

INVENTOR(S) : Michael DeGregorio et al.

It is certified that error appears in the above-identified patent and that said Letters Patent is hereby corrected as shown below:

At Column 2, lines 47 to 48, change "2-[4-(4-chloro-1,2-diphenyl-but-1-enyl)phenoxy]ethanol)" to --Z-2-[4-(4-chloro-1,2-diphenyl-but-1-enyl)phenoxy]ethanol)--.

At Column 2, lines 49 to 50, change "4-[4-chloro-1-[4-(2-hydroxyethoxy) phenyl]-2-phenyl-but-1-enyl]phenol)" to --Z-4-[4-chloro-1-[4-(2-hydroxyethoxy) phenyl]-2-phenyl-but-1-enyl]phenol)--.

At Column 2, lines 51 to 52, change "4-[4-chloro-1-[4-(2-hydroxyethoxy) phenyl]-2-(4-hydroxyphenyl)but-1-enyl]phenol" to --Z-4-[4-chloro-1-[4-(2-hydroxyethoxy) phenyl]-2-(4-hydroxyphenyl)but-1-enyl]phenol--.

Signed and Sealed this

Twenty-seventh Day of February, 2001

NICHOLAS P. GODICI

*Attest:*

*Attesting Officer*   *Acting Director of the United States Patent and Trademark Office*